United States Patent [19]

Ventouras

[11] Patent Number: 4,784,858

[45] Date of Patent: Nov. 15, 1988

[54] CONTROLLED RELEASE TABLET

[75] Inventor: Kimon Ventouras, Le Lignon, Switzerland

[73] Assignee: Zyma SA, Nyon, Switzerland

[21] Appl. No.: 899,112

[22] Filed: Aug. 22, 1986

[30] Foreign Application Priority Data

Aug. 29, 1985 [GB] United Kingdom ............... 8521494

[51] Int. Cl.⁴ .................... A61K 9/22; A61K 9/26; A61K 9/32
[52] U.S. Cl. .................. 424/468; 424/469; 424/470; 424/473; 424/482; 424/488
[58] Field of Search ............... 424/468–470, 424/473, 482, 488

[56] References Cited

U.S. PATENT DOCUMENTS

| | | | |
|---|---|---|---|
| 4,083,949 | 4/1978 | Benedikt | 424/459 |
| 4,155,993 | 5/1979 | Belleville et al. | 424/35 |
| 4,248,858 | 2/1981 | Guley et al. | 424/21 |
| 4,252,786 | 2/1981 | Weiss et al. | 424/19 |
| 4,572,833 | 2/1986 | Pedersen et al. | 424/467 |
| 4,574,080 | 3/1986 | Roswall et al. | 424/458 |
| 4,606,909 | 8/1986 | Bechgaard et al. | 424/469 |
| 4,666,703 | 5/1987 | Kopf | 424/470 |

FOREIGN PATENT DOCUMENTS

| | | |
|---|---|---|
| 153104 | 8/1985 | European Pat. Off. |
| 1468172 | 3/1974 | United Kingdom |
| 2087235 | 5/1982 | United Kingdom |

Primary Examiner—Shep K. Rose
Attorney, Agent, or Firm—Irving M. Fishman

[57] ABSTRACT

A controlled release tablet comprising
(I) a core, containing as essential components
 (a) at least one water-soluble pharmaceutically active substance which is dispersed in a water-insoluble, non-digestible polymeric excipient, and
 (b) a water-insoluble polymeric substance, which is swellable under the influence of water, and
(II) a coating essentially of an elastic, water-insoluble and semipermeable diffusion film of a polymer, is presented, which shows a release pattern for the active substance(s) in a programmed rate of approximately zero order.

15 Claims, 3 Drawing Sheets

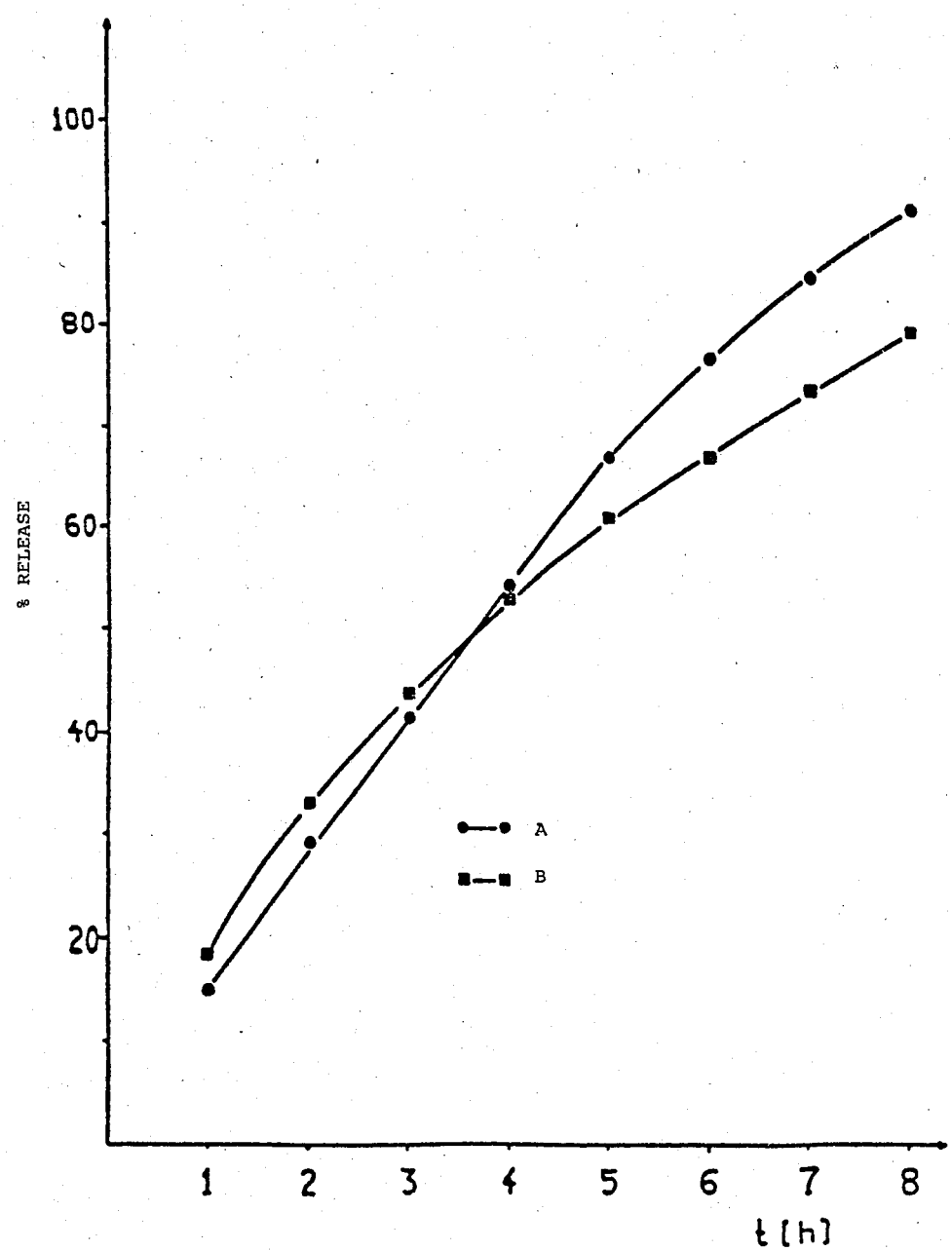

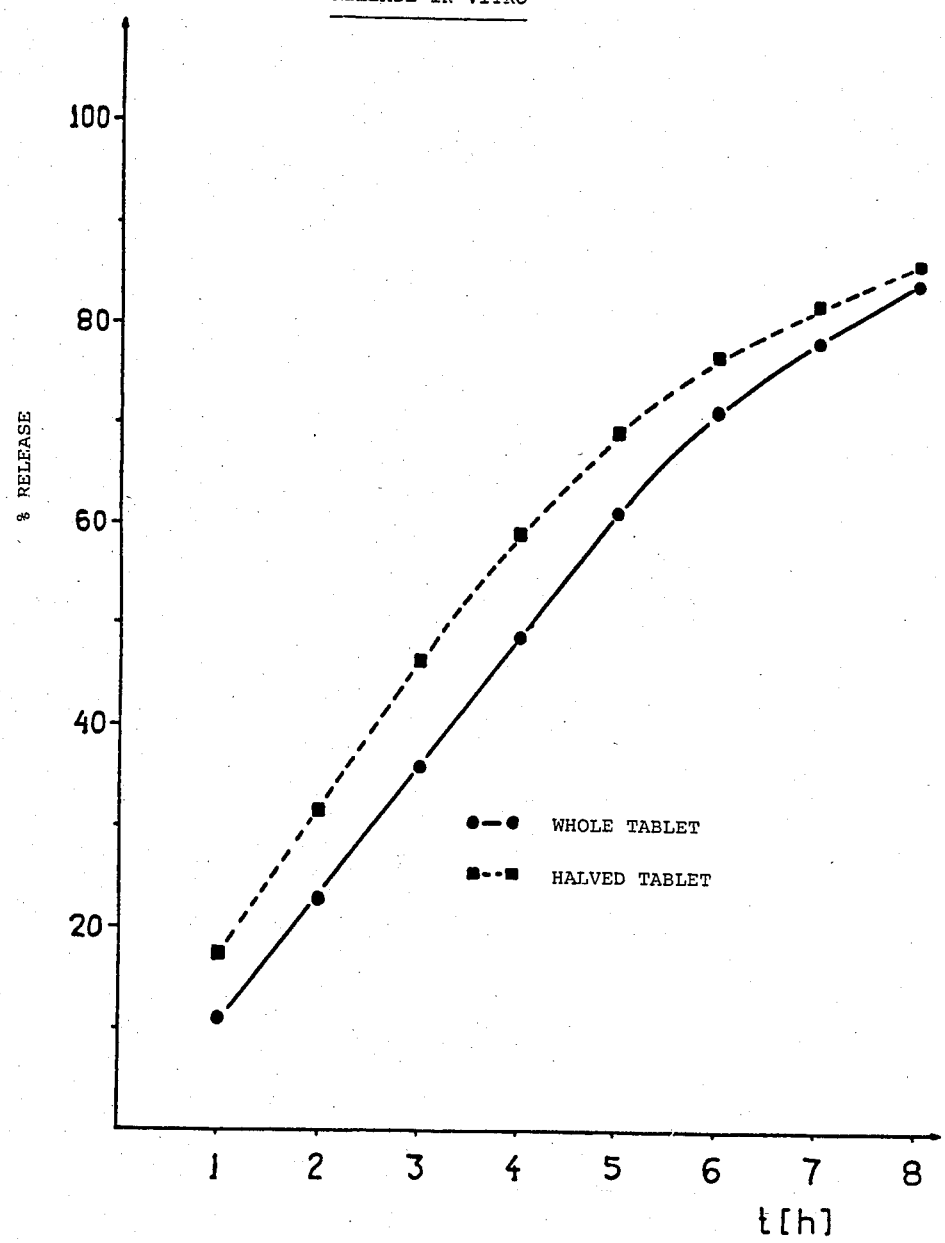

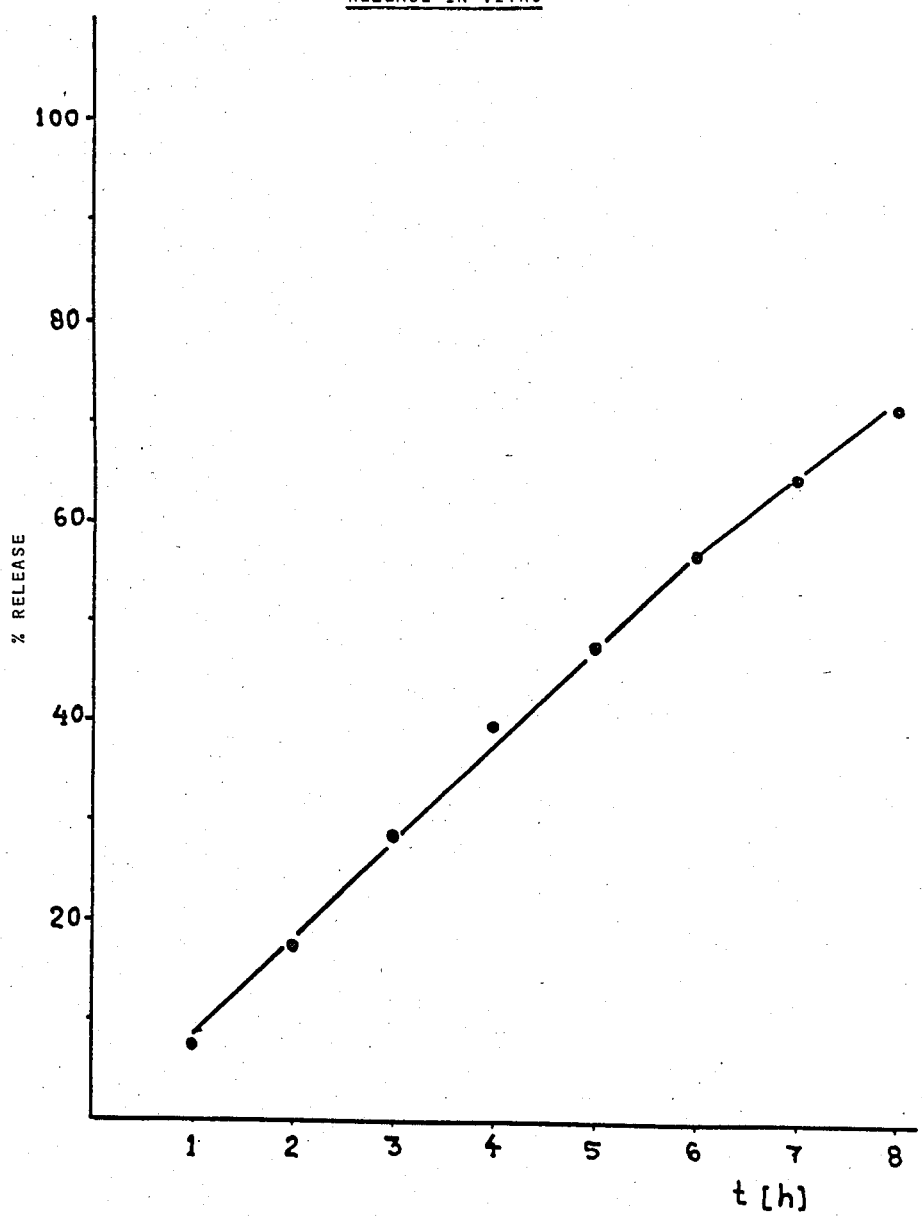

CONTROLLED RELEASE TABLET

The invention relates to a novel improved controlled release tablet, which is useful for the oral administration of pharmaceutically active substances, especially of water-soluble pharmaceutically active substances.

Methods of retarding the release rate of pharmaceuticals have been described in numerous publications. Pharmaceutical preparations adapted for slow release of active substances are usually described as being in retard or depot form.

The ideal oral depot form acts like a permanent intravenous infusion, i.e. it maintains a level of the active substance in the blood which is as constant as possible for the desired duration of activity of the active substance. The goal is thus to obtain a constant release of the active substance at a programmed rate, i.e. a release of approximately zero order, from a tablet for oral intake.

A new, and surprisingly simple, safe and inexpensive formulation for such a controlled release tablet is presented, which shows a release pattern for the active substance(s) in a programmed rate of approximately zero order.

The controlled release tablet according to the present invention comprises (I) a core, containing as essential components
(a) at least one water-soluble pharmaceutically active substance which is dispersed in a water-insoluble, non-digestible polymeric excipient, and
(b) a water-insoluble polymeric substance, which is swellable under the influence of water, and (II) a coating consisting essentially of an elastic, water-insoluble and semipermeable diffusion film of a polymer.

The water-insoluble, non-digestible polymeric excipient in the core of the tablet (Ia) can be for example a water-insoluble plastic polymer, e.g. polyvinylchloride, or preferably a homo- or copolymer of lower alkyl acrylates and/or lower alkyl methacrylates. Here, lower alkyl especially represents methyl or ethyl. Particularly preferred is the ethyl acrylate/methyl methacrylate copolymer, especially in the form of an aqueous dispersion. Most preferred is Eudragit ®-E30D, which is an ethyl acrylate/methyl methacrylate 70:30 (w/w) copolymer having a molecular weight of about 800 000.

The water-insoluble, swellable polymeric substance (Ib) is e.g. a cellulose polymer, such as hydroxypropylmethylcellulose, e.g. Methocel ®-K-15-M, hydroxyethylcellulose, hydroxymethylcellulose, carboxymethylcellulose or sodium carboxymethylcellulose; alginic acid or its sodium salt; or—preferably powdered—cellulose, such as crystalline cellulose, advantageously used in microcrystalline form, such as microcrystaline cellulose commercially available as Avicel ®, e.g. (Avicel PH-102).

The elastic, water-insoluble and semipermeable diffusion film of a polymer (II) essentially consists of e.g. a homo- or copolymer of lower alkyl acrylates and/or lower alkyl methacrylates as described above for the excipient in the core (Ia), preferably alone, or in admixture with the latex (suspension in water) of ethylcellulose, e.g. as sold by FMC Corporation, Philadelphia (Pa./U.S.A.) under the registered trade name Aquacoat ®-ECD-30.

The core as well as the coating may contain usual auxiliaries. Thus, the active substance can be mixed e.g. with a binder like polyvinylpyrrolidone (PVP), e.g. Kollidon ® K-30 (BASF, Ludwigshafen/Rhein, Fed. Rep. Germany), before it is dispersed in the excipient. In addition the core may also contain e.g. a lubricant, such as an alkaline or particularly alkaline earth metal salt of a higher alkanoic acid, such as magnesium stearate or calcium stearate. Auxiliaries of standard quality and acceptability are preferred.

Furthermore, the core may for example contain a pharmaceutically acceptable glidant, e.g. silicon dioxide, such as Aerosil ®-200, which is marketed by Degussa, Frankfurt (Fed. Rep. of Germany). The free flowability of the granules used for preparing the tablet may be improved by this addition.

The coating may contain in addition, e.g. a filler in order to control the permeability of the active ingredient, e.g. a water-soluble filler, such as sodium chloride or a sugar, particularly lactose, fructose or D-mannit, or sorbitol or polyvinylpyrrolidone or a derivative thereof, or dextrane compounds of different molecular weight; or a swellable filler, e.g. hydroxypropylmethylcellulose, hydroxyethylcellulose or hydroxypropylcellulose, e.g. Pharmacoat ®-603, or an antisticking agent, e.g. talcum, or an emulsifier, e.g. polysorbate (Tween ®-80), or a coloring pigment, e.g. indigotin lake or a metal oxide, e.g. iron oxide, such as red iron oxide or yellow iron oxide, or titanium dioxide; or a plasticiser, e.g. polyethylene glycol, such as Lutrol E-400 (BASF).

All pharmaceutically active substances which can be used for oral administration and for which a controlled release in the gastrointestinal tract is desired are essentially suitable, in the form of granules or crystals of an appropriate size, for being processed to a tablet according to the invention. The present invention is however particularly advantageous with respect to the use of active substances which have a narrow therapeutic range because in such cases an approximately zero order release is needed to maintain the level of the active substances in the blood within a desired—therapeutically effective—range. Furthermore, the tablet of the invention is advantageous for the administration of active substances which, when used at a fairly high concentration, can cause local irritation of the mucous lining of the gastro-intestinal tract or other side effects, e.g. vomiting, headache or tremor, and/or which have to be administered in large single doses. Furthermore, it is possible by using the tablet of the invention to decrease the number of administrations per day and thus to increase patience compliance.

This applies for example in the case of potassium chloride administered e.g. in the treatment of hypopotassaemia, or in the case of lithium salts administered e.g. in psychotherapy, or in the case of non-steroidal antiinflammatory drugs, e.g. ibuprofen or pirprofen, or in the case of calcium calts e.g. in the therapy of hypocalcemic states or for calcium supplementation, or in the case of sodium fluoride, e.g. in the treatment of osteoporosis, or in the case of pridinol, or salts thereof, e.g. as a muscle relaxant, or in the case of dimethindene, or salts thereof, e.g. as an antihistaminicum, or in the case of methyl-xanthines, e.g. proxyphylline, diprophylline and/or theophylline, e.g. as bronchodilators, or in the case of a mixture of O-β-hydroxyethylated rutins (Venoruton ®) e.g. in the treatment of venous diseases. All the salts mentioned above must of course be pharmaceutically acceptable so as to be processed according to the invention.

When the tablet according to the invention is in the digestive tract of a patient, the excipient in the core (Ia) and mainly the elastic coating (II) retard the release of the active substance. The polymeric substance (Ib) in the core expands under the influence of water which is penetrating through the coating (II). This in turn extends the surface of the elastic coating and makes it gradually more permeable, whereby the release of the active substance is increased.

BRIEF DESCRIPTION OF THE DRAWINGS

As can be seen from FIG. 1, the release pattern "in vitro" of the active substance of a tablet prepared according to example 1 is approximately of zero order up to 70% release (curve A) in contrast to a tablet which is prepared in the same manner according to example 1 but does not contain a water-insoluble polymeric substance, which is swellable under the influence of water (Ib), in the core (curve B), Also, the halved tablet shows a good zero order release as can be seen from FIG. 2.

FIG. 3 presents the percentage of in vitro released methyl-xanthines.

The tablet according to the invention is manufactured in customary manner by granulating the components of the core in a manner known per se, compressing the granulate obtained to a tablet in a usual table-compressing machine and coating the tablet with the coating material according to known procedures.

The following examples are intended to illustate the invention and are not be be construed as being limitations thereon. Temperatures are given in degrees Centigrade.

EXAMPLE 1

(a) PREPARATION OF THE CORE

A mixture of 1.687 kg proxyphylline, 1.687 kg diprophylline and 1.125 kg of anhydrous theophylline is granulated with 300 g of a 10% w/w solution of polyvinylpyrrolidone in water (0.3 kg dry polyvinylpyrrolidone) in a planetary mixer. The moist mass is forced through a sieve of 2.5 mm mesh width and dried in a fluidized-bed for 20 minutes at 60°. The dried granules are forced through a sieve of 0.71 mm mesh width and then sprayed with 1.500 kg of a 30% aqueous dispersion of 70:30 copolymer of ethyl acrylate and methyl methacrylate (Eudragit ®-E30D) in a fluidized-bed. The spraying speed is 50 g/minute and the inlet air temperature is 30°-35°. The mixture is dried in the same apparatus for 15 minutes at an inlet air temperature of 40°. 0.45 kg of microcrystalline cellulose (Avicel PH-102), 0.025 kg of magnesium stearate and 0.009 kg of colloidal silicon dioxide (Aerosil-200) are added to the granulate obtained. Then the granules are forced through a sieve at 0.71 mm mesh width and are mixed in a planetary mixer for ·15 minutes. The compressing of the granules to form capsule-shaped biconvex tablets each weighing 1.097 g is carried out with the help of a tablet press (KORCH EK-0), having a punch of 21 mm length, 8.5 mm width and a radius of 5.1 mm curvature and a dividing notch to one side.

(b) Preparation of the coating

The coating of 3000 tablets thus obtained is carried out in a coating vessel of 55 cm diameter which is equipped with baffles. With the help of a nozzle, the coating suspension consisting of 0.187 kg of Eudragit ®-E30D, 0.046 kg of lactose, 0.047 kg of talcum, 0.004 kg of polysorbate (Tween ®-80), 1.5 g of indigotin lake and 0.75 g of titanium dioxide in 500 g of water is continuously sprayed on the tablets. The inlet air temperature is 50°; the temperatue of the tablets in the vessel is maintained at approximately 35°. At the end, the coated tablets are dried 10 minutes in the vessel at 40°. The amount of film coating sprayed on is 31 mg (dry weight).

The release rate from these coated tablets (whole and halved tablet) is determined in the dissolution apparatus 2 of the USP XX at 50 rpm in a dissolution medium of pH=1.2 at 37° and measured continuously by UV absorption at 272 nm through a flow cell of 2 mm thickness for the total of methylxanthines released. The release profiles are presented in FIG. 2.

EXAMPLE 2

A mixture of 2812.5 g proxyphylline, 2812.5 g diprophylline and 1875 g of anhydrous theophylline is granulated with 500 g of a 10% w/w solution of polyvinylpyrrolidone in water (0.05 kg dry polyvinylpyrrolidone) in a planetary mixer.

The moist mass is forced through a sieve of 2.5 mm size and dried in a fluidized-bed for 20 minutes at 60°. The dried granules are forced through a sieve of 0.75 mm, then 3020 g of these granules are sprayed with 1000 g of 30% aqueous dispersion of Eudragit ®-E30D in a fluidized-bed. The spraying speed is 50 g/minute and the inlet air temperature is 35°-40°. To 2640 g of these granules are added 168 g of Methocel ®-K-15-M and 13.4 g of magnesium stearate. Then the granules are forced through a sieve of 0.75 mm and mixed in a planetary mixer for 20 minutes. The compressing of the granulate to form round biconvex tablets of 37 mg is carried out with the help of a tablet press (Korch EK-O) having a 10 mm punch and a 7 mm curve radius.

The coating of 2597 g of these tablets is carried out in a coating vessel of 55 cm diameter which is equipped with baffles. With the helf of a nozzle, the coating suspension consisting of 98.81 g of Eudragit ®-E30D, 12.3 g of lactose, 2.06 g of polysorbate (Tween ®-80) and 32.9 g of talcum in 265 g of water is continuously sprayed on the tablets. The inlet air temperature is 50°; the temperature of the tablets in the vessel is maintained at approximately 35°-38°. At the end, the coated tablets are dried for 10 minutes in the vessel at 40°. The amount of film coating per tablet is 11 mg (dry weight).

The percentage of in vitro released methyl-xanthines is determined as described above in example 1 and presented in FIG. 3.

I claim:
1. A controlled release tablet comprising
   (I) a core, containing as essential components
   (a1) at least one water-soluble pharmaceutically active substance;
   (a2) a water-insoluble, non-digestible polymeric excipient being a member of the group consisting of (i) polyvinylchloride and (ii) a homo- or copolymer of lower alkyl acrylates, lower alkyl methacrylates, or lower alkyl acrylate and lower alkyl methacrylate; and
   (b) a water-insoluble polymeric substance which is swellable under the influence of water being a member of the group consisting of hydroxypropylmethylcellulose, hydroxyethylcellulose, hydroxymethylcellulose, carboxymethylcellulose, sodium carboxymethylcellulose, alginic acid, sodium alginate, and cellulose, and

(II) a coating consisting essentially of an elastic, water-insoluble and semipermeable diffusion film of a polymer.

2. A controlled release tablet comprising
(I) a core, containing as essential components
   (a1) at least one water-soluble pharmaceutically active substance;
   (a2) a water-insoluble, non-digestible polymeric excipient being a member of the group consisting of (i) polyvinylchloride and (ii) a homo- or copolymer of lower alkyl acrylates, lower alkyl methacrylates, or lower alkyl acrylate and lower alkyl methacrylate; and
   (b) a water-insoluble polymeric substance which is swellable under the influence of water being a member of the group consisting of hydroxypropylmethylcellulose, hydroxyethylcellulose, hydroxymethylcellulose, carboxymethylcellulose, sodium carboxymethylcellulose, alginic acid, sodium alginate, and cellulose, and
(II) a coating consisting essentially of an elastic, water-insoluble and semipermeable diffusion film of an ethyl acrylate/methyl methacrylate copolymer.

3. The controlled release tablet according to claim 2, wherein said water-soluble pharmaceutially active substance, or one of them, is a member of the group consisting of potassium chloride, lithium salts, non-steroidal antiinflamatory drugs, calcium salts, mixtures of methyl-xanthines, sodium fluoride and O-β-hydroxyethylated rutins.

4. The controlled release tablet according to claim 17, in which the water-insoluble, non-digestible polymeric excipient is an ethylacrylate/methyl methacrylate copolymer.

5. The controlled tablet according to claim 17, in which the water-insoluble polymeric substance which is swellable under the influence of water is cellulose in microcrystalline form.

6. The controlled release tablet according to claim 1, wherein the water-soluble pharmaceutically active substance, or one of them, is a member of the group consistng of potassium chloride, lithium salts, non-steroidal antiinflammatory drugs, calcium salts, mixtures of methyl-xanthines, sodium fluoride and O-β-hydroxyethylated rutins.

7. The controlled release tablet according to claim 1, characterised in that the water-soluble pharmaceutically active substance is potassium chloride.

8. The controlled release tablet according to claim 1, characterised in that the water-soluble pharmaceutically active substance is a lithium salt.

9. The controlled release tablet according to claim 1, characterised in that the water-soluble pharmaceutically active substance is ibuprofen.

10. The controlled release tablet according to claim 1, characterised in that the water-soluble pharmaceutically active substance is pirprofen.

11. The controlled release tablet according to claim 1, characterised in that the water-soluble pharmaceutically active substance is a calcium salt.

12. The controlled release tablet according to claim 1, characterised in that the water-soluble pharmaceutically active substance is sodium fluoride.

13. The controlled release tablet according to claim 1, characterised in that the water-soluble pharmaceutically active substance is a mixture of methyl-xanthines.

14. The controlled release tablet according to claim 1, characterised in that the water-soluble pharmaceutically active substance is a mixture of proxyphylline, diprophylline and theophylline.

15. The controlled release tablet according to claim 1, characterised in that the water-soluble pharmaceutically active substance is a mixture of O-β-hydroxyethylated rutins.

* * * * *